United States Patent [19]

Lee

[11] 4,099,878
[45] Jul. 11, 1978

[54] REMOTE PROBING APPARATUS AND METHOD

[75] Inventor: Robert Wilton Lee, Manton, Calif.

[73] Assignee: Argosystems, Inc., Palo Alto, Calif.

[21] Appl. No.: 744,351

[22] Filed: Nov. 23, 1976

Related U.S. Application Data

[63] Continuation of Ser. No. 562,875, Mar. 28, 1975, abandoned.

[51] Int. Cl.² ............ G01N 71/46; G01N 9/24; G01J 1/00
[52] U.S. Cl. .................... 356/128; 356/129; 73/596; 250/338
[58] Field of Search ............. 181/139, 175; 250/338, 250/573; 356/105, 128, 129; 73/67.6

[56] References Cited

U.S. PATENT DOCUMENTS 3,623,361   11/1971   Funk, Jr. .................. 356/129
3,693,015    9/1972   Funk, Jr. .................. 356/129

OTHER PUBLICATIONS

Nishijima et al., "Moire Patterns: Their Application to Refractive Index and Refractive Index Gradient Measurements", JOSA vol. 54, No. 1, Jan. 1964, pp. 1–5.
Burton; Ralph, "A Modified Schlieren Apparatus for Large Areas of Field", JOSA, vol. 39, No. 11, p. 907, Nov. 1949.

Primary Examiner—Conrad J. Clark

[57] ABSTRACT

Apparatus and method employing line-of-sight wave propagation for measurement of various quantities such as velocity and refractivity structure of a transmission medium at selected locations remote from the measuring device.

22 Claims, 9 Drawing Figures

REMOTE PROBING APPARATUS AND METHOD

This is a continuation, of application Ser. No. 562,875 filed Mar. 28, 1975, now abandoned.

BACKGROUND OF THE INVENTION

This invention relates generally to a method and apparatus for remotely probing a transmission medium to measure quantities such as velocity and refractivity structure and more particularly to such a method and apparatus which propagates a spatially weighted wave through the transmission medium and spatially weights the received wave to generate an electrical signal indicative of the measured quantities at a particular location in the transmission path of the wave.

Only in recent years has interest arisen in the use of line-of-sight wave propagation as a probe of velocity and turbulence in the atmosphere. Probably, this is due to the fact that only in that period has there been sufficient theoretical understanding of propagation in random media.

Radar in its various forms has, of course, long been used for probing atmospheric conditions. Radar, however, is distinguished by the use of pulses or other modulation to achieve distance resolution. The present invention is concerned with a simple, usually continuous-wave transmitter and a separated receiver. As a consequence, other techniques are required to achieve resolution in space.

The theory of weak scattering in media with an irregular refractive index ("star twinkling") was well developed in the 1960's; see, for example, Proceedings of the IEE, Vol. 57, No. 4, April 1969, p. 375, wherein there appears an article co-authored by myself and Mr. Jeffrey C. Harp entitled "Weak Scattering in Random Media, with Applications to Remote Probing." Simple correlation techniques have been used to measure an "average" velocity and turbulence level over the transmission path. In these techniques, the fluctuations from a single transmitter are observed by two spaced receivers and the time delay between the two receiver outputs noted. Such a technique has been recently incorporated into apparatus which is in commercial production.

There is a large interest presently in discriminating among various portions of the propagation path. One method has been the so-called cross-path correlation technique. In this technique two transmitters are used, with a receiver for each. The paths of the two systems are set up to cross at a point of interest. Thus, any similarities in the output of the two receivers usually arise in the vicinity of the path crossing. In August 1973 at the URSI Convention, I described an atmospheric probing method for measuring refractive irregularities and transverse winds employing two wave sources and spatial and temporal filtering.

OBJECTS AND SUMMARY OF THE INVENTION

It is a general object of the present invention to provide an improved remote probing apparatus and method.

It is another object of the present invention to provide a remote probing apparatus in which a single piece of equipment can be used to probe or measure quantities at several locations within the transmission path.

It is a further object of the present invention to provide an apparatus and method which can employ various propagating waves such as radio, optical and acoustic waves.

It is another object of the present invention to provide a method and apparatus which permits the measurement of upper air winds for routing metereological purposes and for aircraft routing.

It is another object of the present invention to provide an apparatus and method suitable for measurement of urban vertical velocity profiles and turbulence profiles for prediction of pollutant transport and mixing.

It is a further object of the present invention to provide a remote probing apparatus and method capable of providing velocity and turbulence profiles in the vicinity of industrial stacks to see if venting should be allowed.

It is a further object of the present invention to provide a method and apparatus which is capable of monitoring aircraft related problems such as airport vortex presence and upper level CAT.

It is another object of the present invention to provide an apparatus and method suitable for specialized metereological research such as research in convection, turbulence, momentum transport, vorticity and the like.

The foregoing and other objects of the invention are achieved with a method and apparatus for measuring various quantities in a transmission medium at various locations in the medium in which means are provided for forming and propagating through the transmission medium under consideration spatially weighted energy waves and means are disposed to receive the spatially weighted energy waves after they have interacted with the quantity, or related quantities, to be measured in the transmission medium, said receiving means serving to spatially weight the received energy wave and generate an output signal indicative of the quantity being measured.

DESCRIPTION OF PREFERRED EMBODIMENTS

Figure 1:
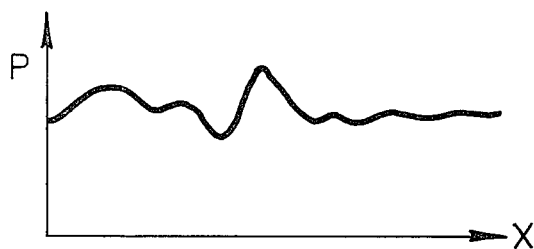
FIG. 1 shows a spatial wave.

Before describing the preferred embodiment of the invention, the concept of spatial filters is set forth. Time filters are familiar. A time filter passes only a certain temporal frequency component when a signal varying with time is input into the filter. Similarly, a spatial filter acts upon a quantity varying over space and passes only a certain spatial frequency. Referring to FIG. 1, there is illustrated a signal whose amplitude P varies over the distance X. This might represent the signal received from a distant transmitter. Just as random voltages have many frequency components, their Fourier decomposition, each of which is a pure sinusoid, the random signal of FIG. 1 has many spatial frequency components, each a sinusoid but in space rather than time. The function of a spatial filter, specifically a narrow band pass spatial filter, is to respond only to one spatial frequency component of the spatial spectrum.

Figure 2:
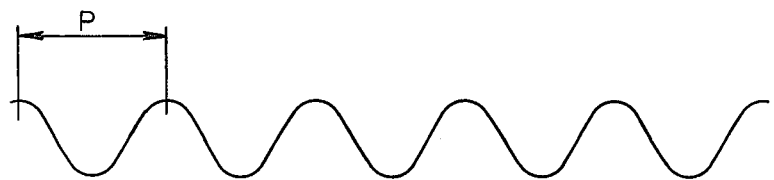
FIG. 2 shows a component of the spatial wave of FIG. 1.
Figure 3:
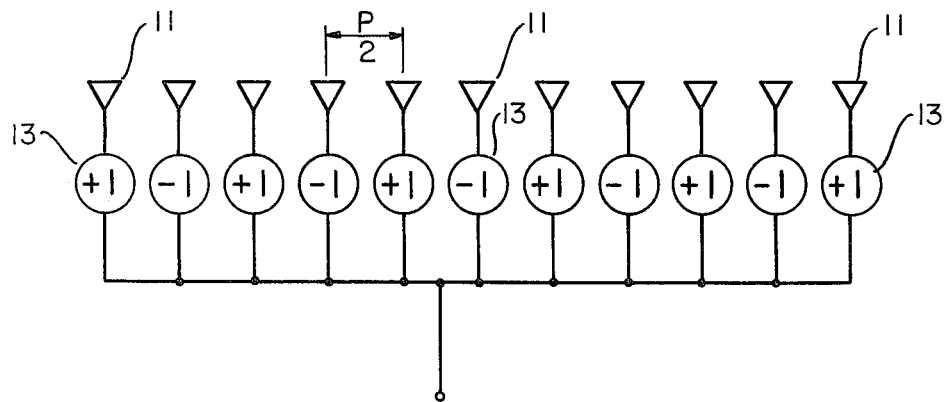
FIG. 3 shows a suitable weighted receiver for receiving a wave such as that of FIG. 1 and detecting a component such as that shown in FIG. 2.

In FIG. 2 one spatial frequency component of the wave of FIG. 1 is illustrated. This sinusoidal component has a period of P meters and a spatial frequency U equal to $2\pi/P$. If a series of receptors 11 is placed at intervals of P/2 and if each is followed by an amplifier 13 with a gain of +1 and −1 alternately, as shown in FIG. 3, and the outputs of the various amplifiers are combined, it can be seen that the output will be quite large. This is because the receptor weighing function +1, −1, etc., matches the spatial sinusoid peak by peak. If the period of the array of receptors is not P/2, this resonance is no longer obtained and the output is nearly zero.

Figure 4:
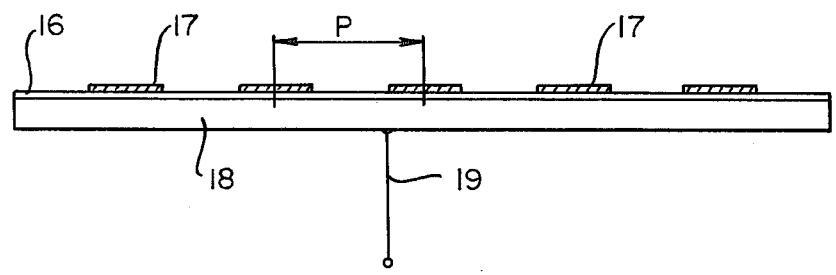
FIG. 4 shows another weighted receiver.

The best weighing function for the filter is not a +1, −1 function, but rather a continuous, sinusoidal weighing function. This may either be achieved approximately using a large number of closely spaced receptors with varying weights, or by using a continuous aperture weighting. For example, a simple intensity mask of parallel dark stripes is appropriate in optical situations. Referring to FIG. 4, a transparent substrate 16 is shown with a plurality of dark stripes 17. A detector 18 serves to receive the energy which is passed. It is to be noted that there will be a high output on the line 19 from the detector in the presence of the spatially weighted wave of FIG. 2, in view of the fact that the dark stripes block out the negative portions of the sinewave while the positive portions are passed by the clear areas.

In practice, the signal intensity is a function of two dimensions, not one. The spatial filter made up of a plurality of strips responds only to one component of the two dimensional spatial spectrum. Thus, one dimensional filters are used hereinafter for illustrative purposes with the assumption that two dimensional filters are usually used.

Weak scattering theory, as described in my paper referred to above, relates the fluctuations observed at the receiver to the fluctuations of the refractive index in the transmission medium. Briefly, it has been shown for weak scattering that the refractive index of the medium may be broken down into its Fourier components and that the effect of these components upon the propagated wave may be considered separately. Each of these Fourier components of refractive index is itself a sinusoid in space and may be thought of as a thin lens with a sinusoidal ripple in one directon such as shown by FC if FIG. 5.

If the lens FC is illuminated by a point source T as shown, a sinusoidal variation in intensity will be observed at the receiver R. Note from the figure that the spatial period of the perturbations at the receiver is larger than that of the Fourier component FC. This is because the perturbations are essentially a shadow. If the Fourier comonent is at the mid-path, the perturbations will be magnified by two. In general, if the path length is L and the perturber is located at the distance S, the magnification factor is L/s.

Figure 5:
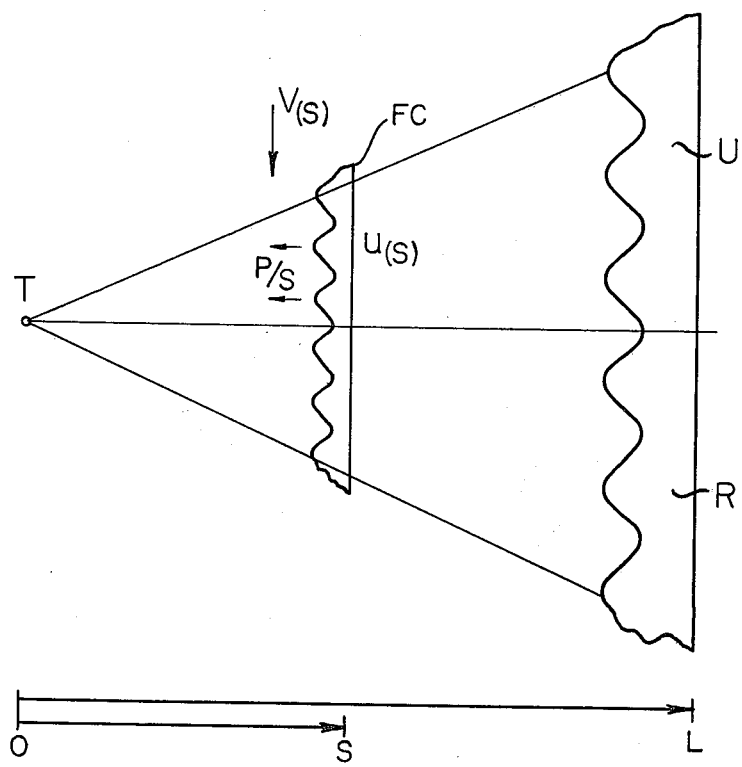
FIG. 5 is a schematic diagram useful in understanding the present invention.

By combining the spatial filter receiver of FIGS. 3 or 4 with the concept of FIG. 5, simply by placing a spatial filter at R in FIG. 5, the following is observed: Since the receiver is now sensitive only to one spatial frequency, say the spatial frequency $U_R$, only one Fourier component FC at location S of frequency $u(s)$, where $u(s) = 2\pi/P(s)$, can contribute to the output of the receiver. The spatial frequency $u(s)$ of the resonant Fourier component must be L/s higher by the multiplication factor mentioned above. We have the constraint that $$u(s) = U_R L/s \tag{1}$$

Figure 6:
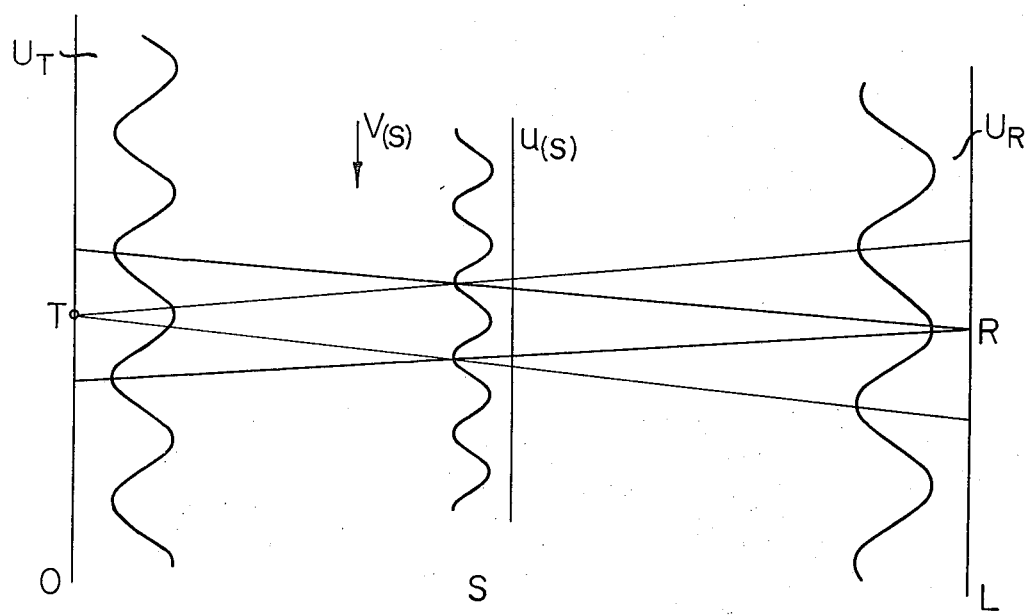
FIG. 6 is another schematic diagram useful in understanding the present invention.

Referring to FIG. 6 and considering radiation from only the point T, the foregoing holds. It is clear that this constraint must also apply to any other source point in the vicinity of the transmitter; that is, only Fourier components with spatial frequencies $u(s)$ which satisfy equation (1) can cause receiver output.

Now reverse the situation and consider only one point at the receiver together with the entire transmitter as a spatial filter (note that we can interchange transmitter and receiver in these discussions). The transmitter spatial filter $U_T$ then imposes a constraint similar to (1) upon $u(s)$ but in this case the magnification works in the opposite direction. To match the transmitter spatial filter $u(s)$ must increase as s nears L or $$u(s) = U_T L/(L-s) \tag{2}$$

Again, this constraint must hold for any point in the vicinity of the receiver. Thus, the allowable $u(s)$, those which can cause receiver output, are constrained by both equations (1) and (2). There is only one solution to these two equations and there is always a solution:

$$u(s) = U_R + U_T \tag{3}$$

$$s/L = 1/(1 + U_T/U_R) \tag{4}$$

Thus, the location of the sensitive point along the path is determined simply by $U_R$ and $U_T$ the resonant spatial frequencies of the spatial filters at the transmitter and at the receiver. The spatial frequency of the Fourier component $u(s)$ is similarly fixed by the spatial filters. The receiver output will fluctuate at a frequency w given by $$w = u(s) \cdot v(s) \tag{5}$$

from which the velocity may be determined. The intensity of the received fluctuation is proportional to the amplitude of the Fourier component. Reference is made to my article appearing in the Journal of the Optical Society of America, Vol.64, No.10, October 1974, for a theoretical explanation of the foregoing principles.

The sense or direction of the velocity $v(s)$ may be obtained by employing two transmitters (or receivers) which are displaced by a distance d which means that at the point s the displacement between the two paths is $d' = d(L-s)/L$ and the time delay $\tau = d'/v(s)$. $\tau$ may be observed as a phase shift $\phi$ at the receiver output. At frequency $w$, $\phi = w\tau$.

Figure 7:
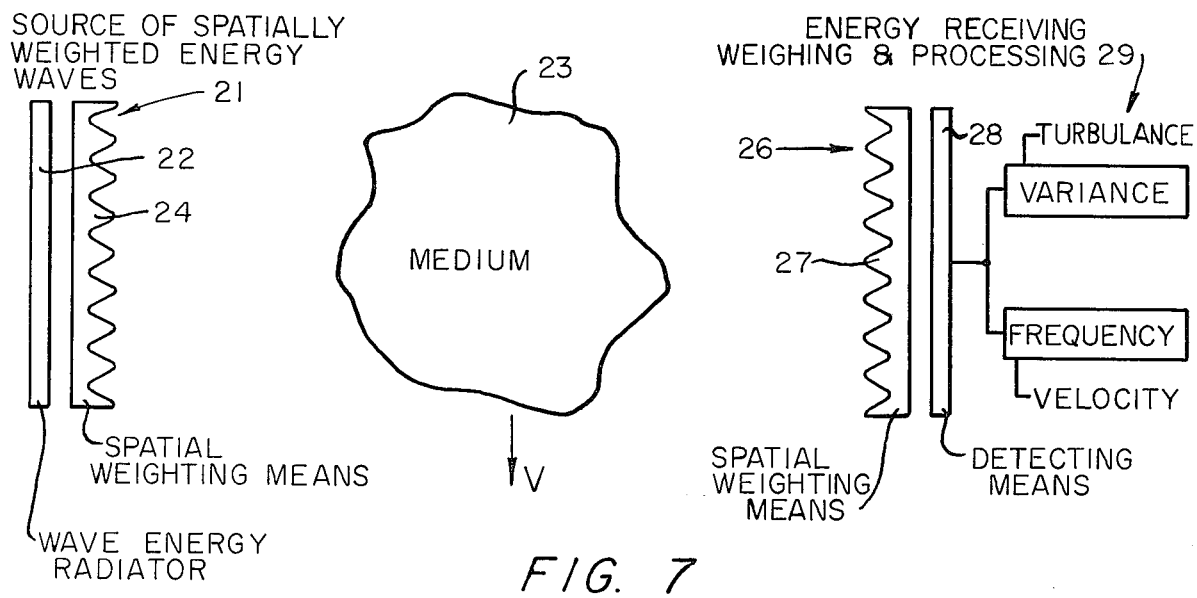
FIG. 7 is a diagram of a generalized apparatus incorporating the present invention.

FIG. 7 shows apparatus suitable for carrying out the present invention. The apparatus comprises a source of spatially weighted energy waves 21 which, as illustrated, includes a source 22 serving to radiate wave energy toward the medium 23 under examination. Spatial weighting means 24 having a predetermined period is interposed between the source and the medium to provide spatially weighted wave energy having a predetermined spatial frequency. The spatially weighted wave energy may be optical or light energy from a suitable light source which is weighted by means of a suitable weighting means such as a filter of the type described above. The filter may also be made from alternate strips of polarizing material which spatially weights the wave by giving it different polarizations. The spatially weighted wave energy may be radio frequency energy applied to an apertured antenna to provide the spatially weighted wave propagating toward the medium. The energy may be sonic energy which is spatially weighted by a filter which selectively absorbs the energy. In any event, there is provided a source of spatially weighted energy of predetermined spatial frequency which is propagated through the medium under consideration.

At the other side of the medium under consideration there is provided an energy receiving, weighting and processing system 26. The system includes means 27 for spatially weighting the received energy, a transducer 28 for receiving the weighted energy and electrical means 29 for providing output signals indicative of parameters under consideration such as turbulence and velocity. In the optical situation, the weighting means and transducing means may be in the form of a plurality of transducers such as shown in FIG. 3 which are suitably spaced and individually weighted. The transducers may be selectively weighted to provide a period which can selectively receive different spatial frequencies to adjust the location of area of the medium along the path between transmitter and receiver which is being examined. The weighting means 27 and transducer 28 may comprise means of the type described in FIG. 4. For the radio frequency and sonic energy, suitable antenna arrays and transducer arrays can provide the required weighting. In any event, there is provided a receiver for the energy which spatially weights the energy and which has a selected period to receive energy of a predetermined spatial frequency. Transducing means convert the energy to an electrical signal which is processed to give information regarding the magnitude of refractivity fluctuations and movement at selected locations in the medium. The location in the medium is determined by the spatial frequency of the transmitted signal and the spatial frequency to which the receiving system is tuned. In the optical system the tuning may be achieved by selectively replacing the filters with filters having the proper spatial frequency for a given point along the path; by electrical means as described with reference to FIG. 3; by making the filter of a material which can be stretched; and by employing lenses in conjunction with the filters. Other methods of providing tunable spatial filters will be apparent to one skilled in the art. Similarly, tunable acoustic and radio frequency filters will be readily realized by persons skilled in the art.

Figure 8:
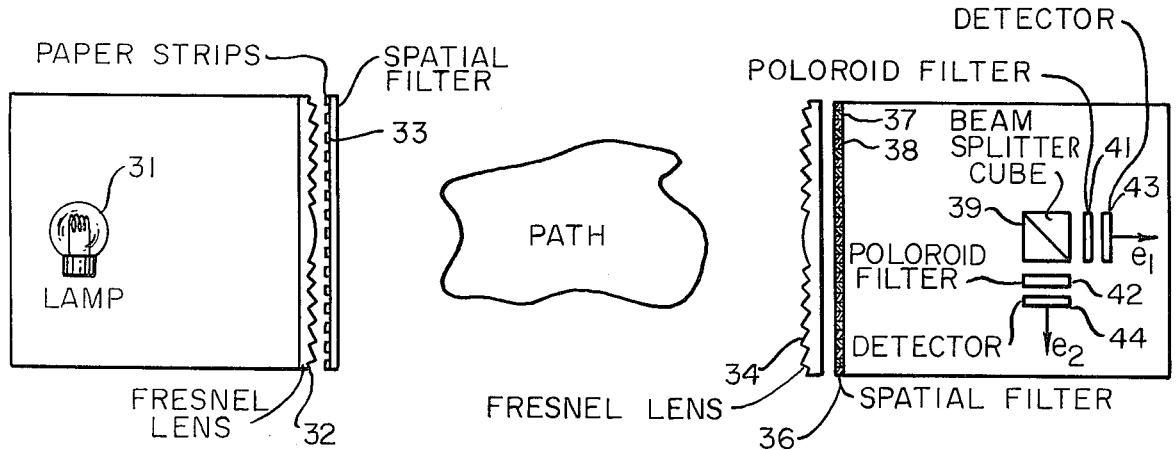
FIG. 8 is a representation of a remote probing apparatus constructed in accordance with the present invention.

Referring to FIG. 8, there is shown an apparatus which was constructed and tested. The transmitter consisted of a small 32-candle power lamp 31 illuminating a plastic Fresnel lens 32 having an aperture of 0.5 × 0.6 meters across. The Fresnel lens was taped with 11 mm wide strips 33 of black paper separated by 11mm. The 28-element spatial filter thus had $U_T = 2\pi/0.022$ m$^{-1}$. Such a positive-only filter was chosen for simplicity as the more desirable zero net weight filter would require more complex apparatus. The receiver was similar in size and resonant wave number with suitable provision made to detect separately with silicon solar cell detectors the energy incident on alternate 11mm wide strips.

The receiver included a Fresnel lens 34 and a filter 36 including polarized strips 37 and 38 orthogonally polarized with respect to one another. The received energy is focused onto a beam splitter 39 after it passes through the filter 36. Polarized filters 41 and 42 of orthogonal polarization are disposed to receive the two outputs from the beam splitter 39. The beams from polarized filters 41 and 42 are applied to transducers 43 and 44, respectively, to give output voltages $e_1$ and $e_2$, respectively.

Figure 9:
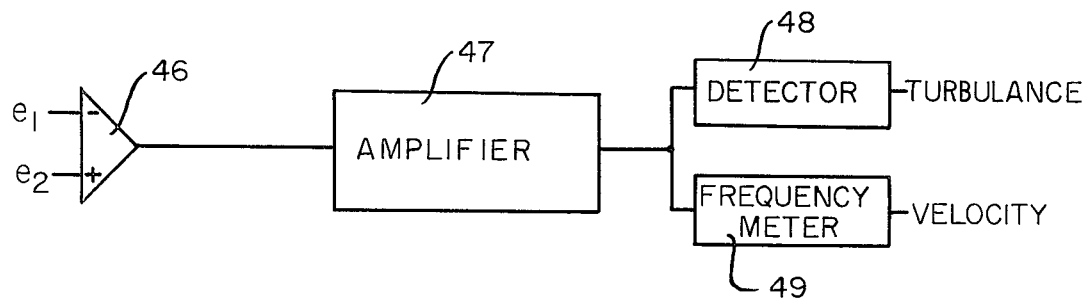
FIG. 9 is a schematic block diagram of the electrical circuits used with the apparatus of FIG. 8.

The output voltages were applied to a subtractor 46, FIG. 9, amplified by a bandpass amplifier 47 (2Hz – 200 Hz). The output of the amplifier was applied to an amplitude detector 48 providing an output voltage proportional to turbulence and to a frequency meter 49 providing an output voltage proportional to velocity.

The path between filters was 61 meters long, 1.5 meters above ground with a theoretical resolution cell at midpoint in the form of an ellipsoid of revolution, 0.5 meters diameter and 0.7 meters long. The light source and detectors were reasonably broad band. The path was instrumented with anemometers to measure transverse winds. An anemometer was placed 0.5 meters from the sensitive point and at other points 3.7 to 15 meters distant. The intensity of the resonant $u$ (with a period of 11 mm) was measured by detecting the output of the receiver which had a bandpass of from 2 L to 200 Ha. The apparent cross-path wind velocity was measured by counting zero crossings of the receiver output. A frequency of 91 Hz was equivalent to 1 meter per second; the time constant of this circuit was about 0.25 seconds.

The experiment was conducted for a 30 hour period, during mostly overcast conditions, with very low and variable winds. Velocities were typically below 1 meter per second at an angle of 30° to the path. The turbulence level (judging from the receiver output) was low and highly intermittent, ranging rapidly over two orders of magnitude. In general, wind velocity as measured by the optical system agreed well with the anemometer measurements made at 0.5 meters away. Light rain and moderate snowfall during portions of the period did not seem to affect performance. Variations in wind records from an anemometer only 3.7 meters distant from the sensitive point showed that the apparatus had a resolution distance of less than 3.7 meters.

It is noted that in the foregoing system only the wind velocity is determined and not the wind sense. If the wind sense is required, a system employing two spaced transmitters is used or equivalently a second receiver is employed.

Thus, it is seen that there has been provided a simple apparatus for measuring refractivity fluctuations, movement and direction at selected distances in a fluid medium through which wave energy can be propagated.

What is claimed is:

1. Apparatus for remote sensing of a refractivity index structure only at a selected region in a fluid transmission medium comprising solely means forming and transmitting spatially weighted divergent propagating waves of energy having a transmit spatial frequency through said fluid medium to interact with said fluid medium and means for receiving and spatially weighting at a receive spatial frequency said waves after transmission through said fluid transmission medium and generating output signals indicative of the refractive index structure, said transmit and receive spatial frequencies determining the selected region between the transmitting means and the receiving means where said refractivity index structure is sensed.

2. Apparatus as in claim 1 wherein said receiving means includes means which provides a signal indicative of the amplitude of said refractivity index structure at said region.

3. Apparatus as in claim 1 wherein said receiving means includes means which provides a signal indicative of the velocity of movement of said refractivity index structure at said location.

4. Apparatus as in claim 1 wherein said receiving means includes means which provides signals indicative of both the amplitude of said refractivity index structure and velocity of movement of said refractivity index structure at said region.

5. Apparatus as in claim 1 wherein said waves of energy are light or infrared waves.

6. Apparatus as in claim 1 wherein said waves of energy are radio waves.

7. Apparatus as in claim 1 wherein said waves are sonic waves.

8. Apparatus for remote sensing of the refractive index structure of a fluid transmission medium only at a selected region comprising a source of divergent light wave energy, means adjacent said source for spatially weighting said light wave energy so that it is transmitted with a predetermined spatial frequency, means directly receiving energy from said transmitter at a predetermined spatial frequency whereby to select the region in the transmission medium where the refractive index structure is observed and means providing an output electrical signal indicative of the refractivity index structure at said region.

9. Apparatus as in claim 8 wherein said means for providing an output signal includes means which provides a signal indicative of the amplitude of said refractivity index structure at said region.

10. Aparatus as in claim 8 wherein said means for providing an output signal includes means which provides a signal indicative of the velocity of movement of said refractivity index structure at said region.

11. Apparatus as in claim 8 wherein said means for providing an outut signal includes means which provides signals indicative of both the amplitude of said refractivity index structure and velocity of movement of said structure at said region.

12. Apparatus as in claim 8 wherein said means for receiving said energy comprises means for spatially weighting said received energy and transducer means for receiving the spatially weighted energy and generating said output signal.

13. Apparatus as in claim 8 wherein the spatial frequency of said receiver or transmitter spatial weighting means can be selectively changed to select the region.

14. Apparatus as in claim 8 wherein said energy receiving means or transmitting means comprises a plurality of transducers which are electrically spatially weighted.

15. Apparatus as in claim 10 including means providing an indication of the direction of said velocity.

16. The method for remote sensing of the refractivity index structure of a fluid transmission medium at a selected location comprising transmitting a spatially weighted diverging propagating wave of energy at predetermined spatial frequency through the fluid medium to interact with the refractivity structure, directly receiving and spatially weighting at a receive spatial frequency the wave after transmission through the fluid medium and generating output signals responsive to the spatially weighted received wave.

17. The method as in claim 16 in which the spatial weighting frequency of the transmitted waves or received waves or both is selected to determine the location in the fluid medium.

18. The method as in claim 17 in which the output signal is indicative of the amplitude of said refractivity index structure at said location.

19. The method as in claim 17 in which the generated signal is indicative of the movement of said refractivity index structure.

20. The method as in claim 16 wherein said waves are light or infrared.

21. The method as in claim 16 wherein the waves are radio waves.

22. The method as in claim 16 wherein the waves are sonic waves.

* * * * *